(12) United States Patent
Omori

(10) Patent No.: US 9,554,827 B2
(45) Date of Patent: Jan. 31, 2017

(54) MEDICAL ROBOT SYSTEM FOR SUPPORTING AN ORGAN IN A POSITION SUITABLE FOR A MEDICAL TREATMENT

(75) Inventor: Shigeru Omori, Ashigarakami-gun (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 1304 days.

(21) Appl. No.: 12/819,522

(22) Filed: Jun. 21, 2010

(65) Prior Publication Data
US 2010/0331859 A1  Dec. 30, 2010

(30) Foreign Application Priority Data
Jun. 24, 2009 (JP) ................. 2009-150119

(51) Int. Cl.
A61B 19/00 (2006.01)
A61B 17/42 (2006.01)
A61B 17/00 (2006.01)

(52) U.S. Cl.
CPC ........... *A61B 17/4241* (2013.01); *A61B 34/30* (2016.02); *A61B 34/37* (2016.02); *A61B 34/71* (2016.02); *A61B 2017/00314* (2013.01); *A61B 2017/00327* (2013.01); *A61B 2017/00464* (2013.01); *A61B 2034/742* (2016.02)

(58) Field of Classification Search
CPC ..... A61B 17/4241; A61B 34/37; A61B 34/71; A61B 34/30; A61B 2034/742; A61B 2017/00327; A61B 2017/00314; A61B 2017/00464

USPC ..... 606/191–193, 130, 119, 215; 604/39–42; 318/568.11, 567; 64/96.01
See application file for complete search history.

(56) References Cited

U.S. PATENT DOCUMENTS

| | | | | |
|---|---|---|---|---|
| 3,833,003 A * | 9/1974 | Taricco | .......................... | 604/509 |
| 5,184,601 A * | 2/1993 | Putman | .......................... | 600/102 |
| 5,520,698 A * | 5/1996 | Koh | .............................. | 606/119 |
| 5,681,340 A * | 10/1997 | Veronikis | ..................... | 606/191 |
| 5,776,144 A * | 7/1998 | Leysieffer et al. | ........... | 606/130 |
| 6,235,037 B1 * | 5/2001 | East et al. | ..................... | 606/119 |
| 6,702,805 B1 * | 3/2004 | Stuart | ............................. | 606/1 |
| 7,453,227 B2 * | 11/2008 | Prisco et al. | ............. | 318/568.11 |
| 2002/0035374 A1 * | 3/2002 | Borillo | ............. | A61B 17/12022 606/194 |
| 2004/0111183 A1 * | 6/2004 | Sutherland | ............. | A61B 19/22 700/245 |
| 2005/0038470 A1 * | 2/2005 | van der Burg | ..... | A61B 17/0057 606/213 |

(Continued)

*Primary Examiner* — Richard Louis
(74) *Attorney, Agent, or Firm* — Whitmyer IP Group LLC

(57) ABSTRACT

Provided is a medical robot system which includes a medical manipulator capable of handling organs such as a uterine of different shapes and sizes. The medical robot system includes a robot arm, a medical manipulator which is detachably provided in the robot arm and supports an organ to a predetermined position, and a controller unit operable by an operator to control the robot arm and the medical manipulator. The medical manipulator also includes a first arm portion in a base side thereof, a second arm portion in a front side thereof for supporting the organ, and a connection portion connecting the first arm portion with the second arm portion. The control unit adjusts a relative direction of the second arm portion and the first arm portion and a length of the second arm portion in a telescopic manner thereby being suitable for organs of various shapes and sizes.

19 Claims, 8 Drawing Sheets

(56) References Cited

U.S. PATENT DOCUMENTS

| | | | |
|---|---|---|---|
| 2005/0228365 A1* | 10/2005 | Wang | A61B 34/75 606/1 |
| 2007/0164696 A1* | 7/2007 | Henne | 318/568.13 |
| 2008/0200836 A1* | 8/2008 | Speeg et al. | 600/567 |
| 2008/0221608 A1* | 9/2008 | Betts | 606/191 |

* cited by examiner

MEDICAL ROBOT SYSTEM FOR SUPPORTING AN ORGAN IN A POSITION SUITABLE FOR A MEDICAL TREATMENT

BACKGROUND

Field

The embodiments discussed herein relate to a medical robot system which includes a medical manipulator for supporting an organ at a predetermined position.

Background Art

In laparoscopic surgery, a patient's abdomen or the like is perforated to make several small holes, an endoscope, forceps, and the like are inserted into the holes, and a surgical operator performs a surgical operation while watching a video of the endoscope through a monitor. In the laparoscopic surgery, in order to facilitate the surgical operation, a treatment target organ or an organ in the vicinity of the treatment target organ is supported at a predetermined position using a medical manipulator.

For example, U.S. Pat. No. 5,520,698 discloses a medical manipulator including a frame which extends in one direction and a tip which includes an expandable balloon and is rotatably connected to a front end of the frame. When the tip is inserted into a uterine cavity and the balloon is expanded, the uterus is supported to a predetermined position.

However, in general, there are differences among individuals in the shapes of organs such as a uterus. For this reason, in the medical manipulator disclosed in U.S. Pat. No. 5,520,698, when the tip is longer than appropriate for the size of the organ, the front end of the tip may come into contact with the organ to thereby damage the organ. On the other hand, when the tip is shorter than appropriate for the size and shape of the organ, the tip may not be disposed at a position where the organ is appropriately supported.

SUMMARY

The present invention is contrived in consideration of the above-described problems, and an object of the invention is to provide a medical robot system which includes a medical manipulator capable of dealing with individual differences in the shape of organs to be supported without increasing in the number of components.

According to a first aspect of the invention, there is provided a medical robot system including: a robot arm; a medical manipulator which is detachably provided in the robot arm and supports an organ from its inside to a predetermined position; and a manipulation unit which is used to manipulate the robot arm and the medical manipulator, wherein the medical manipulator includes: a first arm portion which is provided in a base portion of the medical manipulator; a second arm portion which is located to be closer to a front end of the medical manipulator than the first arm portion and supports the organ; and a connection portion which connects the first arm portion and the second arm portion to each other and is able to change a direction of the second arm portion relative to the first arm portion, and wherein the second arm portion is adapted to be movable in a telescopic manner in the length direction.

In the medical robot system according to the first aspect of the invention, the medical manipulator including the first arm portion and the second arm portion is provided. Accordingly, in the case where the second arm portion is longer than an organ, when the second arm portion is shortened, it is possible to prevent such a problem that the front end of the second arm portion comes into contact with the organ to thereby damage the organ. On the other hand, in the case where the second arm portion is shorter than the organ, it is possible to dispose the second arm portion to an appropriate position by lengthening the second arm portion. Therefore, it is possible to reliably support the organ to a predetermined position. In addition, since it is not necessary to prepare another second arm portion (for example, a tip) having a different length, it is possible to prevent an increase in the number of components. Further, since the medical manipulator is provided in the robot arm, it is possible to further stably support the organ.

According to a second aspect of the invention, in the medical robot system according to the first aspect, the second arm portion is provided with an expandable supporting balloon.

In the medical robot system according to the second aspect of the invention, it is possible to press the supporting balloon against a support target portion (for example, an inner surface of a uterus) of the organ by expanding the supporting balloon. Accordingly, it is possible to easily support the organ.

According to a third aspect of the invention, in the medical robot system according to the first or second aspect, the second arm portion is provided with a fixed portion which is connected to the connection portion and extends in one direction, and a movable portion which is movably fitted to the fixed portion, and the medical robot system further includes a movement mechanism which moves the movable portion in the length direction of the fixed portion.

In the medical robot system according to the third aspect of the invention, since the movable portion is moved in the length direction of the fixed portion by the movement mechanism, it is possible to move the second arm portion in a telescopic manner.

According to a fourth aspect of the invention, in the medical robot system according to any one of the first to third aspects, the first arm portion is provided with an expandable fixing balloon.

In the medical robot system according to the fourth aspect of the invention, it is possible to press the fixing balloon against a portion (for example, an inner surface of a vagina) other than the support target portion by expanding the fixing balloon. Accordingly, since the first arm portion is fixed, it is possible to further stably support the organ compared with the case where the fixing balloon is not provided.

According to a fifth aspect of the invention, in the medical robot system according to any one of first to fourth aspects, the manipulation unit is provided with an input mechanism which is used to operate the medical manipulator, and an input direction of the input mechanism is set to be opposite to a movement direction of the medical manipulator operated by an input operation of the input mechanism.

In gynecology laparoscopic surgery, in the case where a surgical operation is performed on the organ supported by the medical manipulator with facing position, a surgical operator performs the surgical operation while seeing a video of an endoscopic front view of the organ. For this reason, for example, in the horizontal direction, the movement direction of the organ as moved by the medical manipulator is opposite to the movement direction of the organ displayed on the monitor.

Therefore, in the medical robot system according to the fifth aspect of the invention, since the medical robot system is set so that the input direction of the input mechanism is opposite to the movement direction of the medical manipulator, the movement direction of the organ displayed on the monitor is equal to the movement direction of the medical manipulator. For example, the surgical operator may manipulate the input mechanism to the right direction when the organ displayed on the monitor needs to be moved to the right direction, and manipulate the input mechanism to the left direction when the organ needs to be moved to the left direction. Accordingly, it is possible to easily and intuitively dispose the organ displayed on the monitor to a predetermined position.

According to the aspect of the invention, in the case where the second arm portion is longer than the organ, it is possible to prevent such a problem that the front end of the second arm portion comes into contact with the organ to thereby damage the organ by shortening the second arm portion. On the other hand, in the case where the second arm portion is shorter than the organ, it is possible to dispose the second arm portion to an appropriate position by lengthening the second arm portion. Accordingly, it is possible to reliably support the organ to a predetermined position. In addition, since it is not necessary to prepare another second arm portion having a different length, it is possible to suppress an increase in the number of components.

DETAILED DESCRIPTION

As a countermeasure for such problems identified in the Background, it is possible to prepare a plurality of tips having different lengths in advance and to select a tip of an appropriate length in accordance with the shape of the organ to be supported. However, the number of components would have to increase and the exchange operation would be troublesome. Also, in a method of adjusting a position of the tip relative to the organ by reciprocating the medical manipulator, a connection portion between the frame and the tip would move together with the tip. As a result, the tip would not be sufficiently and appropriately rotated depending upon the shape of the organ in some cases.

Hereinafter, a medical robot system according to embodiments of the present invention will be described with reference to FIGS. 1 to 8A and 8B.

First, a medical robot system according to a first embodiment will be described with reference to FIGS. 1 to 7.

Figure 1:
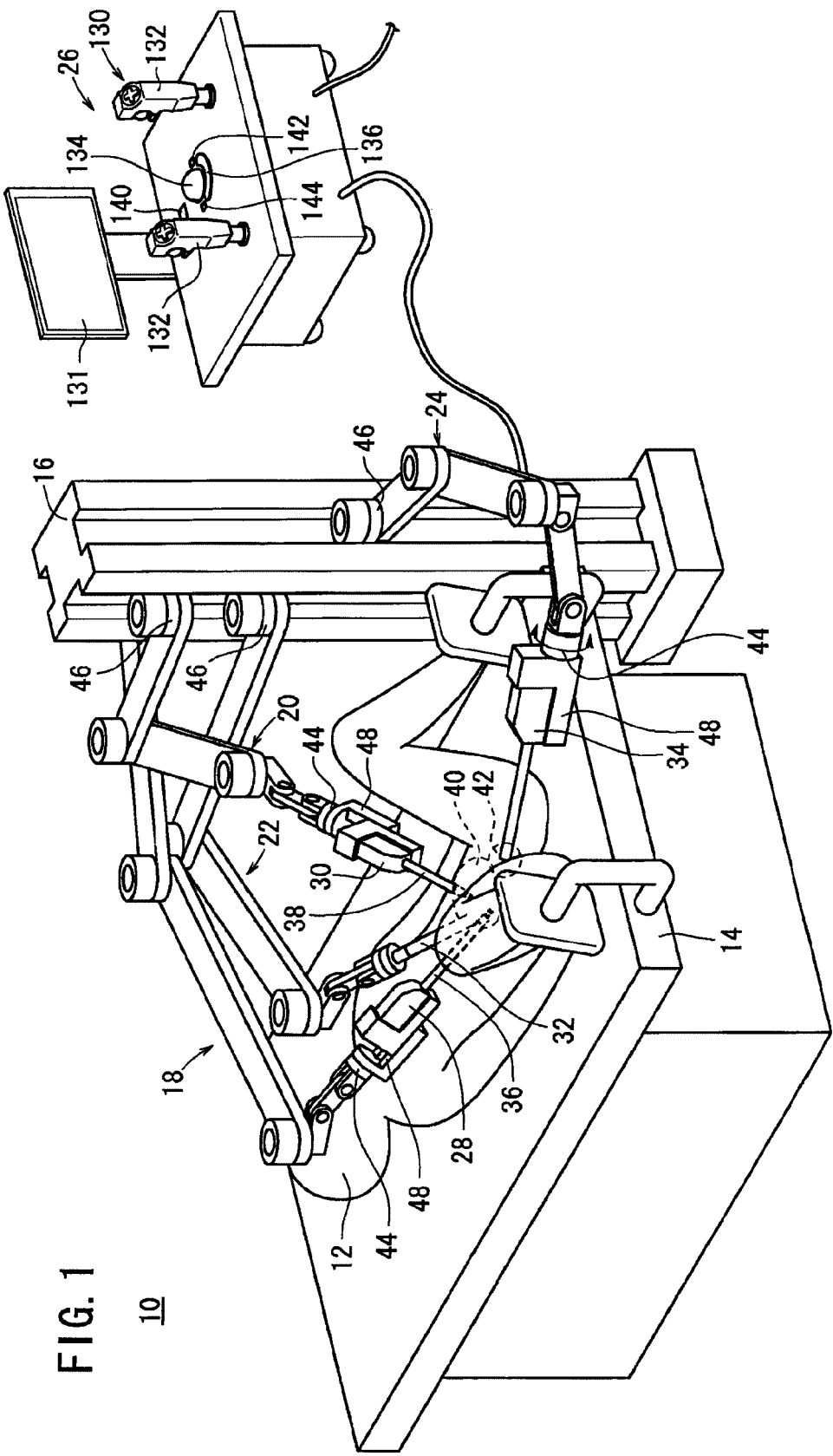
FIG. 1 is a schematic perspective view of a medical robot system according to a first embodiment.

As shown in FIG. 1, a medical robot system 10 includes a uterine manipulator which is a medical manipulator for supporting a uterus of a patient 12 to a predetermined position, and is applied to, for example, a laparoscopic myomectomy (total hysterectomy) of patient 12.

Medical robot system 10 includes a station 16 which is provided in the vicinity of an operating table 14, four units of robot arms 18, 20, 22, and 24 which are provided in the station 16 and each of which has a predetermined mechanism provided in the front end, and a console 26 which performs general control of the entire system. Robot arms 18, 20, 22, and 24 are connected to console 26 through communication channels operated by a wire communication, a wireless communication, a network, or a combination thereof. Console 26 need not be in charge of all the control of the medical robot system 10. For example, each feedback control of robot arms 18, 20, 22, and 24 may be performed on the side of each of robot arms 18, 20, 22, and 24.

The front ends of robot arms 18 and 20 are provided with treatment manipulators 28 and 30, the front end of robot arm 22 is provided with an endoscope 32, and the front end of robot arm 24 is provided with a uterine manipulator 34 as a medical manipulator. Shafts 36 and 38 of treatment manipulators 28 and 30 and endoscope 32 are inserted into a body cavity 40, and uterine manipulator 34 is inserted into a uterine cavity 42 (referring to FIG. 7). Treatment manipulators 28 and 30 and uterine manipulator 34 are detachably provided for robot arms 18, 20, and 24, respectively. As described below, if the manipulators are not particularly distinguished, treatment manipulators 28 and 30 and uterine manipulator 34 are simply referred to as manipulators 28, 30, and 34.

Each of robot arms 18, 20, 22, and 24 includes a multi-link mechanism (for example, an independent six-axis mechanism), and is controlled by console 26 so that manipulators 28, 30, and 34 and endoscope 32 take an arbitrary posture at an arbitrary position within the operation range. Each of the link mechanisms of robot arms 18, 20, and 24 includes a rotation mechanism 44 which rotates each of manipulators 28, 30, and 34, respectively.

Each of robot arms 18, 20, 22, and 24 includes an elevation mechanism 46 which moves along station 16. In addition, each of robot arms 18, 20, and 24 includes a slide mechanism 48 which reciprocates each of manipulators 28, 30, and 34 along the axis of the front end. Robot arms 18, 20, 22, and 24 may have the same configuration, or may have different configurations in accordance with the types of manipulators 28, 30, and 34 and endoscope 32.

Treatment manipulators 28 and 30 are mainly used to perform a direct treatment on patient 12, and front end working portions 28a and 30a (referring to FIG. 7) respectively provided in the front ends of shafts 36 and 38 are provided with, for example, grippers, scissors, electric knives, and the like. Uterine manipulator 34 is used to support the uterus (organ) A to a predetermined position where the surgery is easily performed (referring to FIG. 7).

Figure 2:
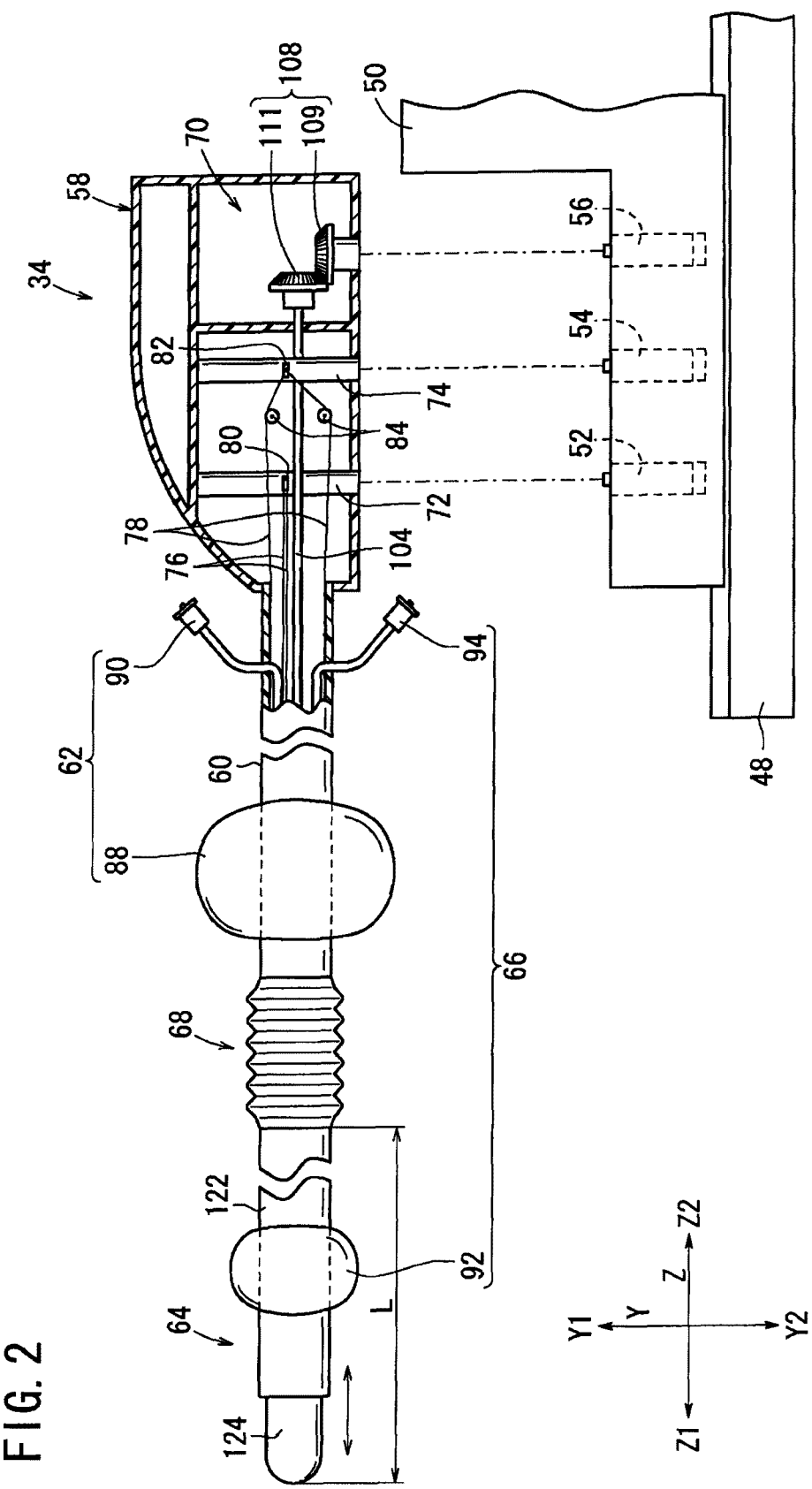
FIG. 2 is a partially sectional side view of a uterine manipulator according to the first embodiment.

Next, a configuration of uterine manipulator 34 and a connection portion between uterine manipulator 34 and robot arm 24 will be described. As shown in FIGS. 2 to 5A and 5B, in uterine manipulator 34, the width direction is set to the X direction, the height direction is set to the Y direction, and the length direction is set to the Z direction. When seen from the base end, the right direction is set to the X1 direction, and the left direction is set to the X2 direction. In FIG. 2, the up direction is set to the Y1 direction, the down direction is set to the Y2 direction, the forward direction is set to the Z1 direction, and the backward direction is set to the Z2 direction.

As shown in FIG. 2, uterine manipulator 34 is detachably provided onto a slider 50 of the front end of robot arm 24. Slider 50 is slidable by slide mechanism 48. Slider 50 is provided with a pair of motors 52 and 54 for curving and a motor 56 for lengthening/shortening which are provided in parallel in the Z direction.

Uterine manipulator 34 includes a base portion 58 which is detachably attached to the slider 50, a first cylindrical arm portion 60 which extends from the base portion 58 in the Z1 direction, a first balloon portion 62 which is provided around first arm portion 60, a second arm portion 64 which is located to be closer to the front end than the first arm portion 60, a second balloon portion 66 which is provided around second arm portion 64, a connection portion 68 which connects first arm portion 60 to second arm portion 64, and a lengthening/shortening mechanism 70 for lengthening or shortening second arm portion 64 in the length direction (insertion direction).

The attachment/detachment operation and the exchange operation of base portion 58 provided onto slider 50 may be performed by a predetermined attachment/detachment mechanism. Base portion 58 is provided with pulleys 72 and 74 which are provided in parallel in the Z direction so as to engage with the pair of motors 52 and 54 for curving. One of motors 52 and 54 for curving, and pulleys 72 and 74, for example, is provided with a non-circular convex portion (not shown), and the other is provided with a concave portion (not shown) which engages with the convex portion, thereby transmitting the rotation of motors 52 and 54 for curving to pulleys 72 and 74.

Figure 3:
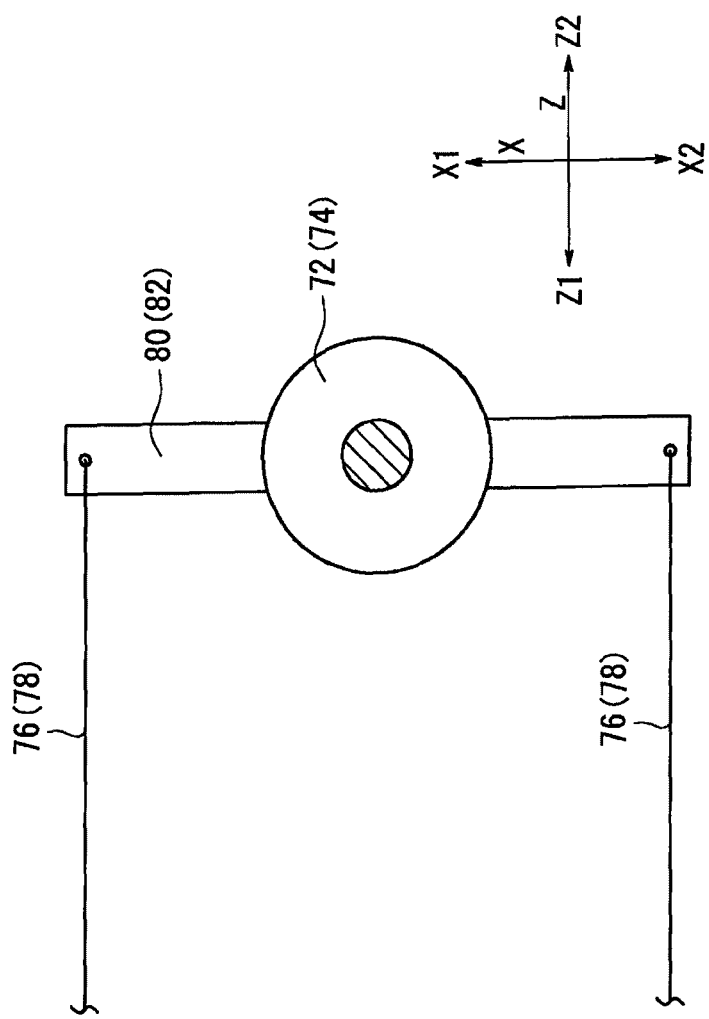
FIG. 3 is a plan view of a pulley and an arm.

As shown in FIGS. 2 and 3, pulleys 72 and 74 respectively include arms 80 and 82 which are connected to wires 76 and 78 and extend in the X direction. When pulleys 72 and 74 rotate, one of two wires 76 and 78 extending in the horizontal direction is wound, and the other is drew out. Here, since wires 76 and 78 are not wound around pulleys 72 and 74, neither of pulleys 72 and 74 has a function of a pulley in a strict sense, but they are called pulleys for convenience of description.

As shown in FIG. 2, the inside of base portion 58 is provided with a pair of idlers 84 and 84 which guides wire 78 from arm 82 into first arm portion 60. Each of the pair of idlers 84 and 84 is disposed at the inclined vertical position (a direction between the Z1 direction and the Y1 direction and a direction between the Z1 direction and Y2 direction) with respect to the arm 82 of the pulley 74, and guides wire 78 into first arm portion 60.

As shown in FIG. 2, first balloon portion 62 includes a first balloon 88 which is an expandable balloon for supporting and a first fluid supply portion 90 which supplies a fluid to first balloon 88. Second balloon portion 66 includes a second balloon 92 which is an expandable balloon for fixing formed to be smaller than first balloon 88 and a second fluid supply portion 94 which supplies a fluid to second balloon 92. First balloon 88 is disposed in the vicinity of connection portion 68, and second balloon 92 is disposed in the vicinity of the front end of second arm portion 64 (referring to FIG. 7). First and second balloons 88 and 92 are made of, for example, a flexible and/or elastic material such as rubber. As a fluid supplied to first and second balloons 88 and 92, for example, air or sterilized natural saline solution is used.

Figure 4:
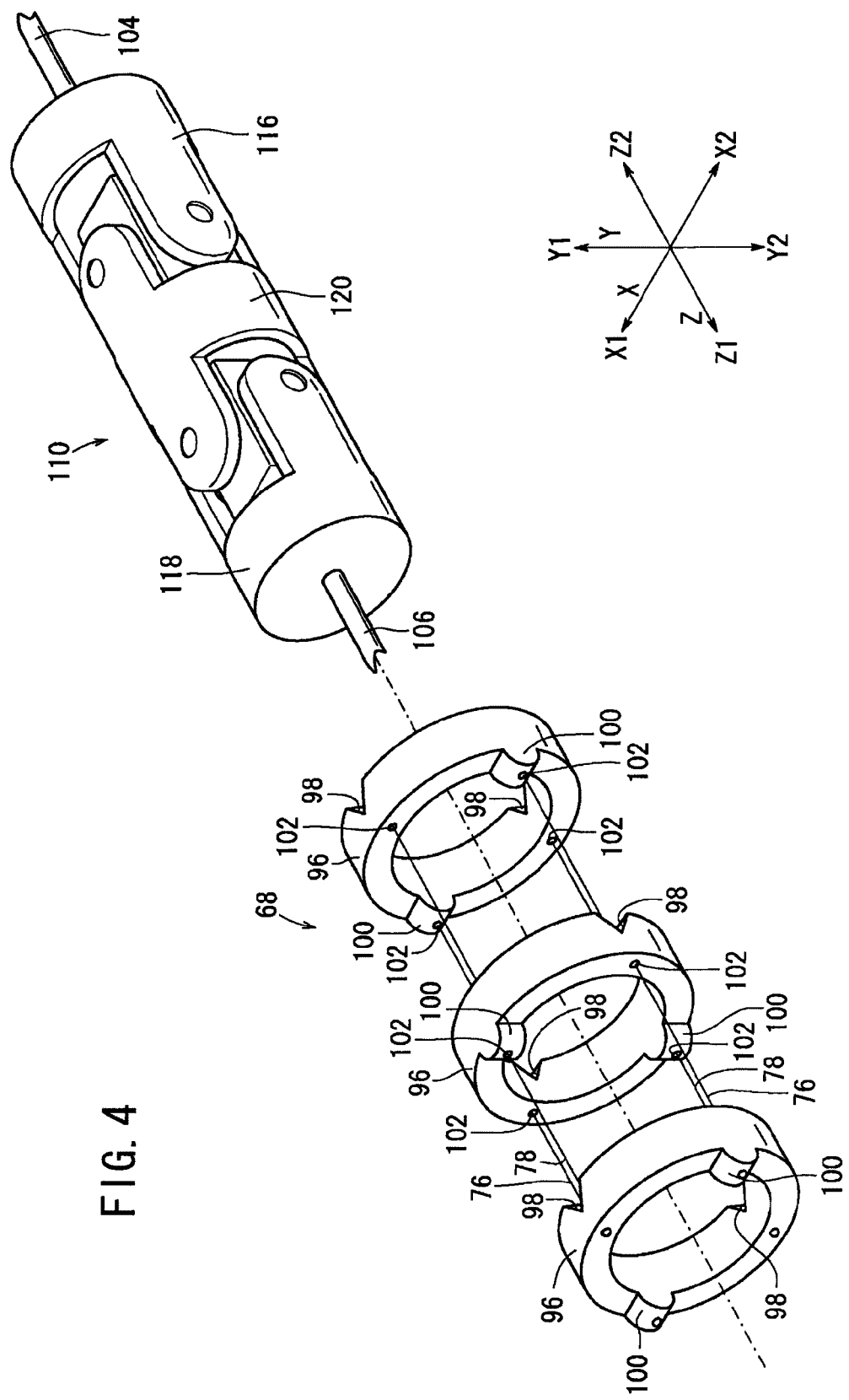
FIG. 4 is an exploded perspective view of a connection portion.

As shown in FIG. 4, connection portion 68 has a configuration in which a plurality of joint rings 96 are stacked so as to be rotatable relative to each other. In addition, in FIG. 4, connection portion 68 is described as comprising three joint rings 96, but the number of provided joint rings 96 is not limited thereto. For example, the number of joint rings 96 may be approximately four to thirty.

One surface of each of joint rings 96 is provided with a pair of V-shaped grooves 98 facing each other around the center of joint ring 96, and the other surface thereof is provided with a pair of semi-circular protrusion portions 100 facing each other around the center of joint ring 96 so as to be located at a position 90° out of phase from grooves 98. In this case, adjacent joint rings 96 are disposed so as to have the position of grooves 98 90° out of phase from each other. Joint rings 96 are stacked to each other in such a manner that both protrusion portions 100 of one joint ring 96 are respectively inserted into both facing grooves 98 of the other joint ring 96.

In addition, in each of joint rings 96, perforation holes 102 are respectively provided at the positions of both grooves 98 and both protrusion portions 100. Wires 76 and 78 are respectively inserted through perforation holes 102 corresponding to each of joint rings 96, and the front ends of wires 76 and 78 are connected to joint ring 96 which is disposed on the front end side (Z1 side) of connection portion 68. Accordingly, joint rings 96 are collected so as to be substantially integrated with each other.

In connection portion 68, since a gap is formed between adjacent joint rings 96 in the state where protrusion portions 100 are inserted in grooves 98, the protrusion portions 100 are rotatable in the inside of grooves 98, and hence the adjacent joint rings 96 are rotatable relative to each other. In this case, a rotation angle between a pair of adjacent joint rings 96 is small, but when plural angles of plural pairs of joint rings 96 are accumulated, a desired curve of the entire curving portion can be obtained, and the direction of second arm portion 64 with respect to first arm portion 60 is changeable.

Thus, when pulleys 72 and 74 are appropriately rotationally driven under the control of console 26, each of wires 76 and 78 are reciprocated by a predetermined distance, thereby curving connection portion 68 by a desired angle in the vertical and horizontal directions in the transverse section of first arm portion 60. That is, connection portion 68 is actively bent or curved by an operation of pulling wires 76 and 78. In this case, the curving direction or the degree of freedom is not particularly limited. In addition, although it is not shown in the drawings, the outer periphery of each joint ring 96 may be coated by, for example, a coating film made of an elastic or flexible material.

As shown in FIGS. 2, 4, 5A, and 5B, lengthening/shortening mechanism 70 includes a first rod portion 104 which is located inside first arm portion 60, a second rod portion 106 which is located inside second arm portion 64, a gear mechanism 108 which is provided in the base end of first rod portion 104 and transmits the rotation of lengthening/shortening motor 56 to the first rod portion 104, a joint portion 110 which is located inside joint ring 96 and connects first rod portion 104 and second rod portion 106 to each other, and a screw portion 114 which is provided in the front end of second rod portion 106 with a stopper portion 112 therebetween.

As understood from FIGS. 2 and 4, first rod portion 104 is formed to be longer than first arm portion 60, and extends to the inside of base portion 58 so as to be connected to gear mechanism 108. As understood from FIGS. 4, 5A, and 5B, second rod portion 106 is formed to be slightly shorter than second arm portion 64.

As shown in FIG. 2, gear mechanism 108 located inside base portion 58 includes a first bevel gear 109 which engages with lengthening/shortening motor 56 and a second bevel gear 111 which is connected to first rod portion 104 and engages with first bevel gear 109.

As shown in FIG. 4, joint portion 110 is configured as a so-called universal joint including a first pin portion 116 which is connected to first rod portion 104, a second pin portion 118 which is connected to second rod portion 106, and an intermediate member 120 which connects first pin portion 116 and second pin portion 118 to each other. In addition, in FIG. 4, one intermediate member 120 is exemplified for the description. However, the number of provided intermediate members 120 is not limited thereto, but may be plural.

Intermediate member 120 is connected to first pin portion 116 and second pin portion 118 so as to be movable in two directions (the X and Y directions in FIG. 4) perpendicular to the movement direction of intermediate member 120. Accordingly, it is possible to bend joint portion 110 in the transverse section of first arm portion 60 in the vertical and horizontal directions by a desired angle. That is, it is possible to change the direction of second rod portion 106 with respect to first rod portion 104. As a result, in the case where connection portion 68 is bent, it is possible to bend joint portion 110 in accordance with the bending operation of connection portion 68.

Figure 5A:
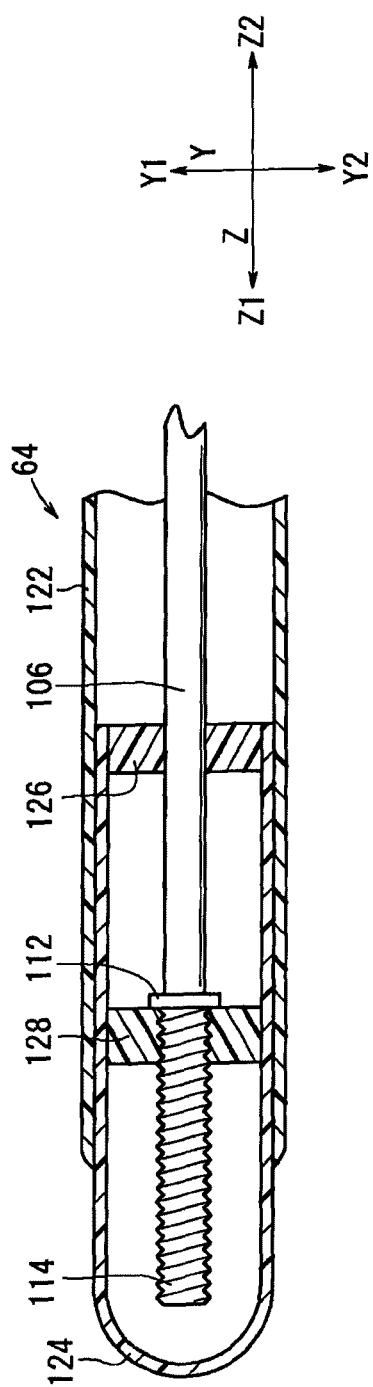
FIG. 5A is a sectional view illustrating a shortened state of a second arm portion according to the first embodiment.
Figure 5B:
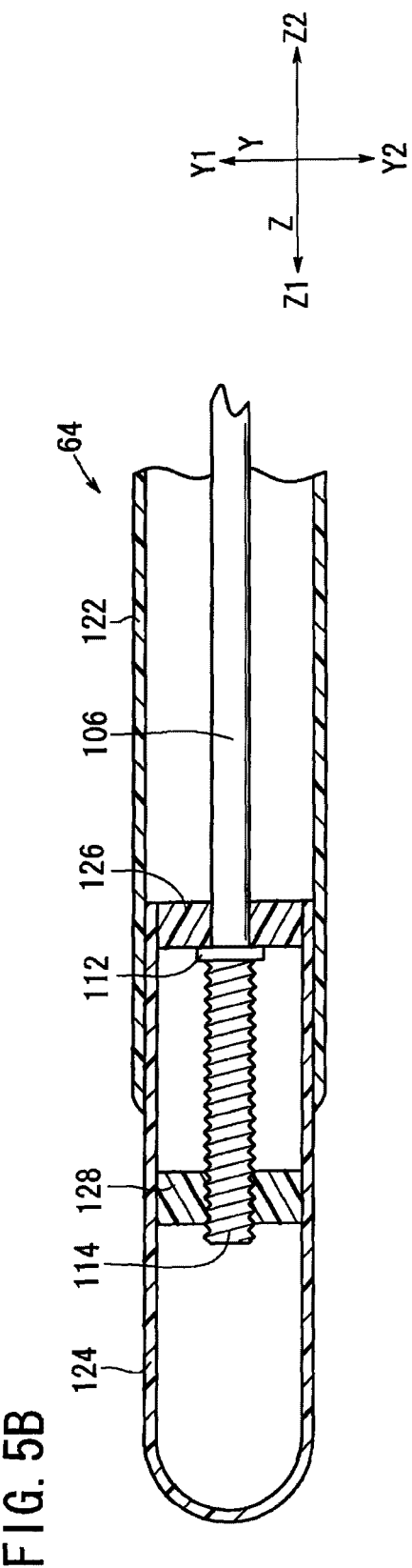
FIG. 5B is a sectional view illustrating a lengthened state of the second arm portion according to the first embodiment.

As shown in FIGS. 5A and 5B, second arm portion 64 includes a cylindrical stationary portion 122 (referring to FIG. 2) which is connected to connection portion 68 and a hollow movable portion 124 which is fitted to the front end of fixed portion 122 and is slidable in the length direction of fixed portion 122.

Screw portion 114 and stopper portion 112 are located inside movable portion 124. One end (front end) of movable portion 124 is formed as a hemispherical shape, and the other end of movable portion 124 is fixed with a limitation member 126 which allows stopper portion 112 to come into contact therewith. In addition, movable portion 124 is provided with a nut portion 128 which is threaded into screw portion 114 so as to be movable in the length direction of stationary portion 122.

Accordingly, when first bevel gear 109 is rotated under the control of console 26, second bevel gear 111, first rod portion 104, joint portion 110, second rod portion 106, stopper portion 112, and screw portion 114 are rotated together, thereby moving nut portion 128 in the length direction of stationary portion 122. That is, second arm portion 64 is movable in a telescopic manner in the length direction. In addition, the movement of movable portion 124 in a direction in which second arm portion 64 is shortened is limited in such a manner that nut portion 128 comes into contact with stopper portion 112 (referring to FIG. 5A), and the movement of movable portion 124 in a direction in which second arm portion 64 is lengthened is limited in such a manner that stopper portion 112 comes into contact with limitation member 126 (referring to FIG. 5B). The length of screw portion 114 for determining the movement distance of movable portion 124 may be arbitrarily set in consideration of the depth of a uterus of a typical patient, for example.

As shown in FIG. 1, console 26 is provided with a manipulation unit 130 which is used to manipulate the operations of robot arms 18, 20, and 24, treatment manipulators 28 and 30, and uterine manipulator 34, and with a monitor 131 which is used to display information such as an image captured by endoscope 32 thereon.

Figure 6:
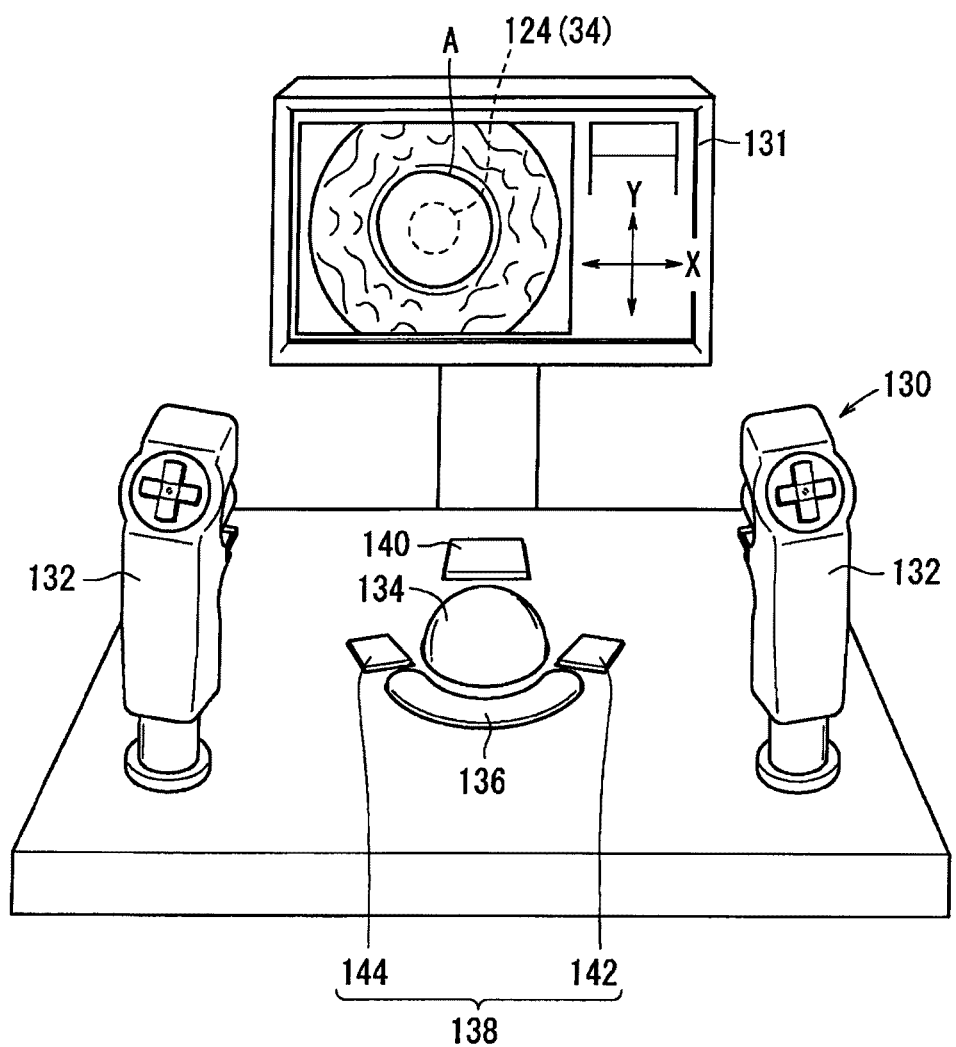
FIG. 6 is a schematic perspective view of a console.

As shown in FIG. 6, manipulation unit 130 includes two joysticks 132 and 132 which are provided at left and right positions where the joysticks are easily manipulated by both hands, a trackball 134 which is input means provided to be close to the center, a safety switch 136 which is disposed to be close to trackball 134 while substantially surrounding the half of the circumference thereof, a lengthening/shortening control switch 138 which is disposed to be close to safety switch 136, and a return switch 140. Joysticks 132 are configured to manipulate robot arms 18 and 20 and treatment manipulators 28 and 30. Robot arm 22 and endoscope 32 may be manipulated by another input means (not shown). Trackball 134 is configured to manipulate robot arm 24 and uterine manipulator 34.

Lengthening/shortening control switch 138 includes a first switch 142 which rotates lengthening/shortening motor 56 so that movable portion 124 moves in the Z1 direction (a direction in which second arm portion 64 is lengthened) shown in FIG. 5B, and a second switch 144 which rotates lengthening/shortening motor 56 so that movable portion 124 moves in the Z2 direction (a direction in which second arm portion 64 is shortened) shown in FIG. 5A.

Trackball 134 and lengthening/shortening control switch 138 are set to be manipulated only while safety switch 136 is being pushed. Accordingly, it is possible to prevent the movement of uterine manipulator 34 even when the operator contacts trackball 134 by mistake. Return switch 140 is a switch which returns uterine manipulator 34 to a predetermined position, for example, a position in uterus A where uterine manipulator 34 is initially inserted.

When trackball 134 is manipulated in the horizontal direction, the vertical direction, and the rotation direction, second arm portion 64 of uterine manipulator 34 moves in the horizontal direction and the vertical direction in accordance with the manipulation, and entire uterine manipulator 34 rotates. In medical robot system 10, the manipulation direction of trackball 134 is set to be opposite to the movement direction of uterine manipulator 34. Specifically, in medical robot system 10, the manipulation direction of trackball 134 is set to be same as the movement direction of uterine manipulator 34 in the vertical direction (Y direction), and the manipulation direction of trackball 134 is set to be opposite to the movement direction of uterine manipulator 34 in a direction including the component in the horizontal direction (the X direction).

Figure 7:
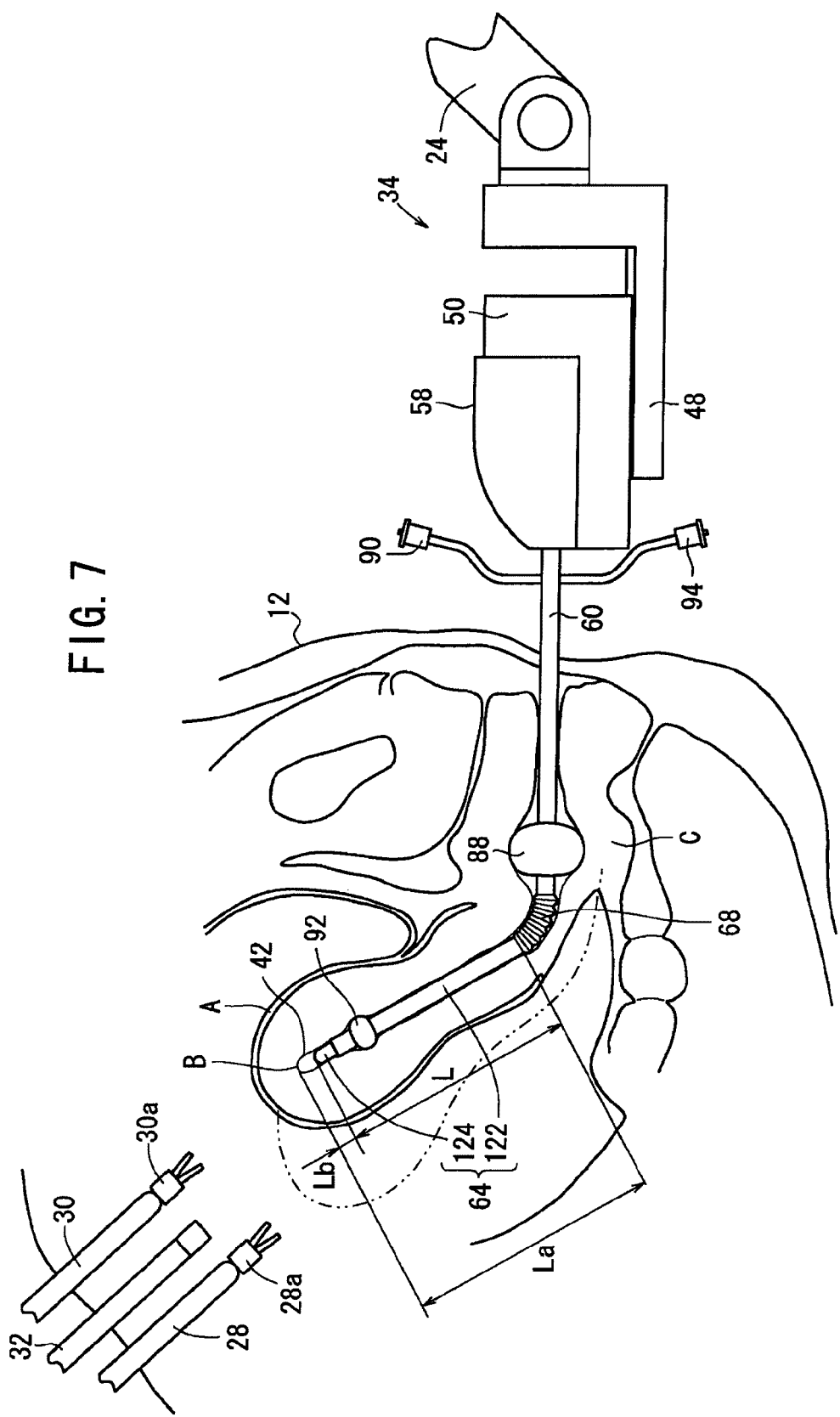
FIG. 7 is a diagram showing a state where a uterus is supported to a predetermined position.

That is, in medical robot system 10 according to the embodiment, as shown in FIG. 7, since the video image from endoscope 32 disposed at a position facing uterus A is displayed on monitor 131, the movement direction of uterus A displayed on monitor 131 is opposite to the actual movement direction of uterus A supported by the uterine manipulator 34 in the horizontal direction.

Therefore, as described above, it is possible to allow the horizontal movement direction of uterus A displayed on monitor 131 to be equal to the manipulation direction of trackball 134 by setting the manipulation direction of the trackball 134 to be opposite to the horizontal movement direction of uterine manipulator 34. Accordingly, the surgical operator may manipulate trackball 134 to the right direction when uterus A displayed on monitor 131 needs to be moved to the right direction, manipulate trackball 134 to the left direction when uterus A needs to be moved to the left direction, manipulate trackball 134 to the inclined right-up direction when uterus A needs to be moved to the inclined right-up direction, and manipulate trackball 134 to the inclined left-down direction when the uterus A needs to be moved to the inclined left-down direction. Accordingly, it is possible to easily and intuitively dispose uterus A displayed on monitor 131 to a desired position.

Next, an operation of uterine manipulator 34 will be described with reference to FIG. 7 in the case of a uterine myoma, for example.

First, first and second balloons 88 and 92 are maintained in a shortened state, and uterine manipulator 34 is inserted into uterine cavity 42 of patient 12 so that connection portion 68 is disposed at a predetermined position.

At this time, in the case where length L of second arm portion 64 is longer than uterus depth La (L>La), second arm portion 64 is shortened by manipulating second switch 144. Accordingly, it is possible to prevent such a problem that uterus A is damaged due to a contact of the front end of movable portion 124 with respect to uterus bottom B, and to easily ensure an optimal gap Lb. On the other hand, in the case where second arm portion 64 is shorter than uterus depth La ({La-L}>Lb), second arm portion 64 is lengthened by manipulating first switch 142. Accordingly, it is possible to dispose second arm portion 64 to an appropriate position inside uterus cavity 42. That is, in the state where uterine manipulator 34 is inserted to be disposed at an appropriate position, it is possible to form a predetermined gap Lb between the front end of movable portion 124 and uterus bottom B. It is desirable that predetermined gap Lb is set in the range of, for example, 0.5 cm to 1.0 cm.

When the insertion operation of uterine manipulator 34 is completed, a fluid is supplied from first and second fluid supply portions 90 and 94 to first and second balloons 88 and 92 so as to expand first and second balloons 88 and 92. Accordingly, since first balloon 88 is pressed against the inner surface of vagina C and second balloon 92 is pressed against the inner surface of uterus A, first balloon 88 is fixed to vagina C, and second balloon 92 is fixed to uterus A. Stationary portion 122 and the portion other than the front end of movable portion 124 may come into contact with the inner surface of uterus A. In this case, since the contact area between second arm portion 64 and the inner surface of uterus A increases, it is possible to improve stability of uterine manipulator 34.

Subsequently, uterus A is disposed and supported to a position where a treatment thereof is easily performed in such a manner that second arm portion 64 is moved by manipulating trackball 134. Accordingly, the uterine myoma is supported within an operation range of endoscope 32 and treatment manipulators 28 and 30. Then, the uterine myoma is removed in such a manner that treatment manipulators 28 and 30 are moved by manipulating joysticks 132.

In medical robot system 10 according to the embodiment, since it is possible to dispose uterine manipulator 34 to an appropriate position inside uterine cavity 42 by lengthening or shortening second arm portion 64 of uterine manipulator 34 in the longitudinal direction (insertion direction), it is not necessary to prepare a plurality of second arm portions (tips) 64 having different lengths. For this reason, it is possible to avoid an increase in the number of components. In addition, since second balloon 92 is provided in second arm portion 64, it is possible to easily support uterus A through second balloon 92.

In addition, since first balloon 88 is fixed to vagina C, it is possible to change the direction of second arm portion 64 by using first balloon 88 serving as a fulcrum. Accordingly, it is possible to more stably support uterus A through uterine manipulator 34 than in the case where first balloon 88 is not provided. In addition, since uterine manipulator 34 according to the embodiment is manipulated while being connected to robot arm 24 under the control of console 26, in the case of the surgery lasting for a long time, it is possible to stabilize uterine manipulator 34 better than in the case where uterine manipulator 34 is manipulated by human hands.

Next, a uterine manipulator 234 according to a second embodiment will be described with reference to FIGS. 8A and 8B. In the second embodiment, the same reference numerals are given to the same constituents as those of the first embodiment, and the description thereof is omitted. In addition, FIGS. 8A and 8B correspond to FIGS. 5A and 5B.

Figure 8A:
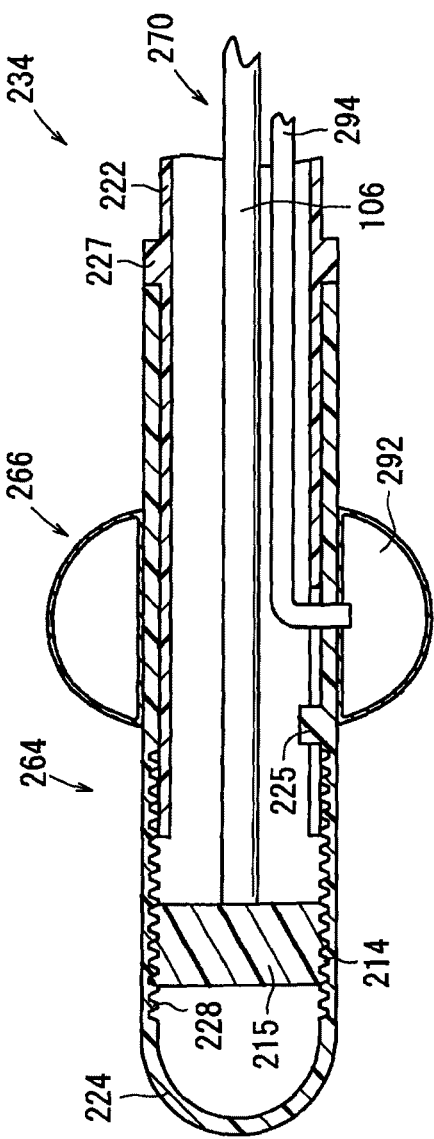
FIG. 8A is a sectional view illustrating a shortened state of the second arm portion of the uterine manipulator according to a second embodiment.
Figure 8B:
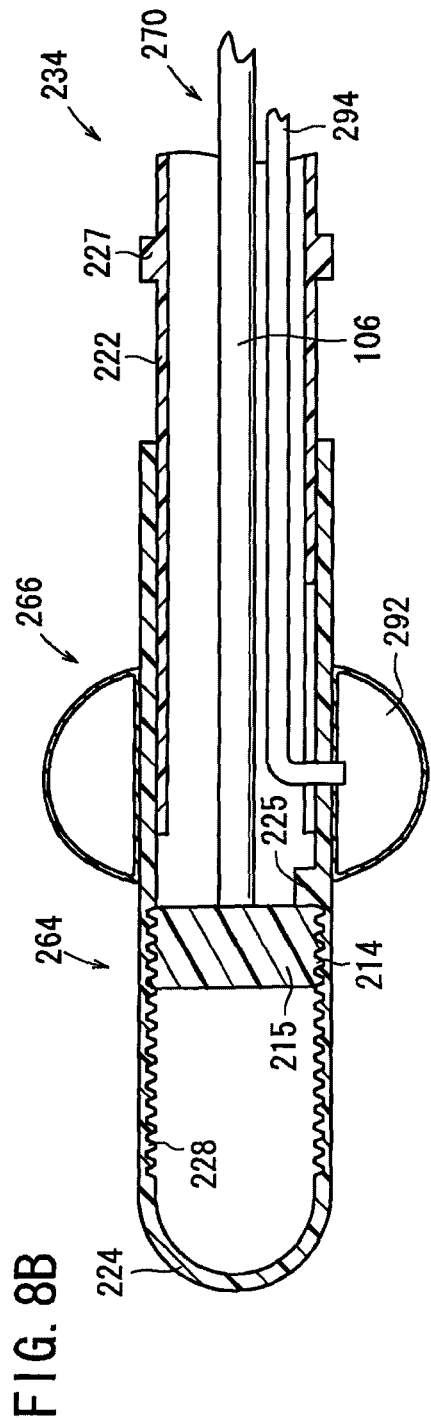
FIG. 8B is a sectional view illustrating a lengthened state of the second arm portion of the uterine manipulator according to the second embodiment.

As shown in FIGS. 8A and 8B, in the second embodiment, a configuration of a second arm portion 264, a second balloon portion 266, and a lengthening/shortening mechanism 270 is different from that of the first embodiment. In detail, second arm portion 264 includes a stationary portion 222 and a movable portion 224 which is fitted around the outside of stationary portion 222 so as to be slidable in the longitudinal direction of stationary portion 222. Stopper portion 112 and limitation member 126 of the first embodiment are omitted, and there are further provided a first limitation member 225 which is provided in the inner surface of movable portion 224 and a second limitation member 227 which is provided in the outer surface of stationary portion 222. In addition, a second balloon 292 is provided around movable portion 224, and a front end member 215 including a first screw portion 214 is provided in the front end of second rod portion 106. A second screw portion 228 is provided in the inner surface of movable portion 224 so as to engage with first screw portion 214. The front end of stationary portion 222 is provided with a notch (hole) within which a second fluid supply portion 294 and first limitation member 225 can move as movable portion 224 moves.

In the embodiment having the above-described configuration, when first bevel gear 109 is rotated under the control of console 26, second bevel gear 111, first rod portion 104, joint portion 110, second rod portion 106, and front end member 215 are rotated together, thereby moving movable portion 224 in the longitudinal direction of stationary portion 222. That is, second arm portion 264 moves in a telescopic manner in the longitudinal direction. In addition, the movement of movable portion 224 in a direction to shorten second arm portion 264 is limited in such a manner that movable portion 224 comes into contact with second limitation member 227 (referring to FIG. 8A), and the movement of movable portion 224 in a direction to lengthen second arm portion 264 is limited in such a manner that front end member 215 comes into contact with first limitation member 225 (referring to FIG. 8B). The length of second screw portion 228 may be arbitrarily set as in the case of screw portion 114 according to the first embodiment.

In the second embodiment, since second balloon 292 is provided around movable portion 224, it is possible to change the relative position of second balloon 292 with respect to first arm portion 60 when movable portion 224 is moved in the longitudinal direction of stationary portion 222. Accordingly, since it is possible to move second balloon 292 to a position where uterus A is easily supported, it is possible to more stably support uterus A.

In the above-described embodiments, the position of second arm portion disposed inside the vagina of the uterus may be adjusted after expanding the first balloon on the side of the first arm portion. In this case, since the first balloon is fixed to the vagina, it is not possible to adjust the position of the second arm portion inside the uterine cavity in the case of the uterine manipulator in which the second arm portion cannot be shorten and lengthen in a telescopic manner, for example, the uterine manipulator in which the length of the second arm portion is adjusted by exchanging a plurality of second arm portions having different lengths. However, in the uterine manipulator according to the above-described embodiments, since it is possible to shorten and lengthen the second arm portion in a telescopic manner, it is possible to adjust the position of the second arm portion inside the uterine cavity even after having expanded the first balloon.

The invention is not limited to the above-described preferred embodiments, but may be modified into various forms within the scope of the spirit of the invention.

For example, in the medical manipulator according to the invention, at least any one of the first and second balloons may be omitted. In the case where the second balloon is omitted, a subject organ is supported to a predetermined position in the state where the portion other than the front end of the second arm portion comes into contact with the subject organ. In addition, the position of the first balloon relative to the first arm portion and the position of the second balloon relative to the second arm portion may be arbitrarily set. In the medical manipulator according to the invention, the invention is not limited to the example in which only one connection portion is provided, but a plurality of connection portions may be provided. The subject organ where the medical manipulator according to the invention is used is not limited to the uterus. For example, the medical manipulator may be used in other organs such as the stomach or intestine (large intestine). The joint portion of the lengthening/shortening mechanism is not limited to the example in which a universal joint is used, but may be formed in, for example, a bellows shape.

What is claimed is:

1. A medical robot system comprising:
    a first robot arm;
    a medical manipulator, detachably connected to said first robot arm, to support an organ at a predetermined position in a patient body, said medical manipulator including:
        a first arm portion provided on a proximal side of said medical manipulator,
        a second arm portion, provided on a distal side of said medical manipulator relative to said first arm portion, to support the organ, said second arm portion including
            a hollow first member, and
            a hollow second member that is concentric with the first member such that walls of the second member are slidably accommodated with walls of the first member, and
        a bendable connection portion disposed on a distal end of said first arm portion so as to connect said first arm portion with said first member of said second arm portion, an entirety of said first and second members of said second arm portion being disposed distally of said connection portion, and a directional orientation of said second arm portion being adjustable relative to said first arm portion via said connection portion;
    a control unit to adjust a longitudinal extension of said second arm portion within the organ, and to adjust the directional orientation of said second arm portion relative to said first arm portion; and
    an expandable supporting balloon provided on said second arm portion.

2. The medical robot system according to claim 1, wherein said first member of said second arm portion is a stationary portion connected to said connection portion, the stationary portion extending in a longitudinal direction,
    wherein said second member of said second arm portion is a movable portion movably fitted to said stationary portion, and
    wherein said medical robot system further comprises a movement mechanism to move said movable portion relative to said stationary portion in the longitudinal direction thereof.

3. The medical robot system according to claim 2, wherein said second arm portion further comprises a stopper mechanism to limit a relative movement of said stationary portion and said movable portion within a predetermined range.

4. The medical robot system according to claim 3, wherein the stopper mechanism is disposed within the second member of the second arm portion.

5. The medical robot system according to claim 2, wherein said control unit comprises:
    an input switch to control said movement mechanism to cause a relative movement of said stationary portion and said movable portion to adjust the longitudinal extension of said second arm portion, and
    a safety switch, and
    wherein said input switch is manipulable only when said safety switch is actuated.

6. The medical robot system according to claim 2, further comprising an expandable supporting balloon provided on said movable portion of said second arm portion.

7. The medical robot system according to claim 1, further comprising an expandable fixing balloon provided on said first arm portion.

8. The medical robot system according claim 1,
    wherein said control unit comprises an input mechanism to operate said medical manipulator, and
    wherein said control unit controls said medical manipulator in such a manner that an input movement direction of said input mechanism is opposite to an actual horizontal movement of said medical manipulator.

9. The medical robot system according to claim 1, further comprising:
    a second robot arm; and
    a treatment manipulator, detachably connected with said second robot arm, to apply a medical treatment to the organ supported by said second arm portion.

10. The medical robot system according to claim 9, further comprising:
    a third robot arm; and
    an endoscope, detachably connected with said third robot arm, to capture an image of the organ supported by said second arm portion,
    wherein said control unit includes a monitor to display an image captured by said endoscope.

11. The medical robot system according to claim 1, wherein an exterior surface of the walls of the second member slides against an interior surface of the walls of the first member.

12. The medical robot system according to claim 11, wherein the longitudinal extension of said second arm portion is adjusted via a limitation member and a threaded nut portion through which a correspondingly threaded screw portion passes, the limitation member and the nut portion being housed within the second member.

13. The medical robot system according to claim 1, wherein an interior surface of the walls of the second member slides against an exterior surface of the walls of the first member.

14. The medical robot system according to claim 13, wherein the longitudinal extension of said second arm portion is adjusted via rotation of a threaded front end member disposed within the second member that abuts a threaded wall portion of the interior surface of the walls of the second member, the front end member being attached to a rod that extends through the first member.

15. The medical robot system according to claim 14, wherein the first member includes a notch in the walls thereof through which a fluid supply extends to fill an expandable supporting balloon disposed on the second member.

16. A medical robot system comprising:
a robot arm;
a medical manipulator, detachably connected to said robot arm, to support an organ at a predetermined position in a patient body, said medical manipulator including:
an arm portion provided on a proximal side of said medical manipulator,
a support for supporting the organ, said support provided on a distal side of said medical manipulator relative to said arm portion, said support including
a hollow first member, and
a hollow second member that is concentric with the first member such that walls of the second member are slidably accommodated with walls of the first member, and
a joint for connecting said arm portion with said first member of said support, said joint being disposed on a distal end of said arm portion, an entirety of said first and second members of said support being disposed distally of said joint, and a directional orientation of said support being adjustable relative to said arm portion via said joint; and
a controller for adjusting a longitudinal extension of said support within the organ, and for adjusting the directional orientation of said support relative to said arm portion;
wherein an interior surface of the walls of the second member slides against an exterior surface of the walls of the first member.

17. The medical robot system according to claim 16, further comprising an expandable supporting balloon provided on said support.

18. A medical robot system comprising:
a robot arm;
a medical manipulator, detachably connected to said robot arm, to support an internal portion of an organ at a predetermined position in a patient body, said medical manipulator including:
an arm portion provided on a proximal side of said medical manipulator;
a support for supporting the organ, said support provided on a distal side of said medical manipulator relative to said arm portion, said support including
a hollow first member, and
a hollow second member that is concentric with the first member such that walls of the second member are slidably accommodated with walls of the first member, and
a joint for connecting said arm portion with said first member of said support, said joint being disposed on a distal end of said arm portion, an entirety of said first and second members of said support being disposed distally of said joint, and a directional orientation of said support being adjustable relative to said arm portion via said joint; and
a controller driving one or more motors for adjusting a longitudinal extension of said support within the organ, and for adjusting the directional orientation of said support relative to said arm portion.

19. The medical robot system according to claim 18, further comprising an expandable supporting balloon provided on said support.

* * * * *